(12) United States Patent
Mitra et al.

(10) Patent No.: US 6,920,351 B2
(45) Date of Patent: Jul. 19, 2005

(54) NEURAL PROSTHETIC USING TEMPORAL STRUCTURE IN THE LOCAL FIELD POTENTIAL

(75) Inventors: Partha Mitra, Summit, NJ (US); Bijan Pesaran, Los Angeles, CA (US); Richard A. Andersen, La Canada, CA (US)

(73) Assignee: California Institute of Technology, Pasadena, CA (US)

(*) Notice: Subject to any disclaimer, the term of this patent is extended or adjusted under 35 U.S.C. 154(b) by 0 days.

(21) Appl. No.: 10/304,343

(22) Filed: Nov. 25, 2002

(65) Prior Publication Data

US 2003/0078522 A1 Apr. 24, 2003

Related U.S. Application Data

(62) Division of application No. 09/738,875, filed on Dec. 14, 2000, now Pat. No. 6,615,076.
(60) Provisional application No. 60/170,861, filed on Dec. 14, 1999.

(51) Int. Cl.$^7$ .............................................. A61B 5/04
(52) U.S. Cl. ...................................... 600/544; 600/545
(58) Field of Search ................................ 600/300–301, 600/544–546, 372, 578; 623/24–25, 27, 57, 61

(56) References Cited

U.S. PATENT DOCUMENTS

| | | | |
|---|---|---|---|
| 5,178,161 A | * | 1/1993 | Kovacs ........................ 607/115 |
| 5,365,939 A | | 11/1994 | Ochs |
| 5,368,041 A | | 11/1994 | Shambroom |
| 5,638,826 A | * | 6/1997 | Wolpaw et al. ............. 600/544 |
| 5,692,517 A | * | 12/1997 | Junker ........................ 600/545 |
| 5,748,845 A | * | 5/1998 | Labun et al. .................. 706/10 |
| 6,171,239 B1 | * | 1/2001 | Humphrey ................... 600/372 |
| 6,516,246 B2 | * | 2/2003 | Derakhshan ................ 700/245 |
| 6,609,017 B1 | * | 8/2003 | Shenoy et al. .............. 600/372 |

OTHER PUBLICATIONS

Salinas et al. "Transfer of Coded Information from Sensory to Motor Networks" J. Neurosci. 1995 15:6461–6474.*

Venkatesh N. Murthy and Eberhard E. Fetz; Oscillatory Activity in Sensorimotor Cortex of Awake Monkeys: Synchronization of Local Field Potentials and Relation to Behavior; Dec. 1996; Journal of Neurophysiology, vol. 76, No. 6, pp. 3949–3967.

(Continued)

*Primary Examiner*—Robert L. Nasser
*Assistant Examiner*—Patricia Mallari
(74) *Attorney, Agent, or Firm*—Fish & Richardson P.C.

(57) ABSTRACT

In an embodiment, neural activity of a subject may be measured with an implant in the sensory motor cortex of the subject and used to predict an intended movement. The measured neural activity may be the local field potential (LFP) at an electrode or single unit (SU) activity. The spectral structure of the LFP and the SU activity may be estimated using spectral analysis techniques. The estimated LFP and SU responses may be used to predict and intended movement by the subject.

33 Claims, 11 Drawing Sheets

OTHER PUBLICATIONS

Kechen Zhang, Iris Ginzburg, Bruce L. McNaughton, and Terrence J. Sejnowski; Interpreting Neuronal Population Activity by Reconstruction: Unified Framework with Application to Hippocampal Place Cells; vol. 79, No. 2, pp. 1017–1044.

Jerome N. Sanes and John P. Donoghue; Oscillations in Local Field Potentials of the Primate Motor Cortex During Voluntary Movement; May 1993; Proc. Natl. Acad. Sci.. USA, vol. 90, pp. 4470–4474.

Alexander V. Lukashin, Bagrat R. Amirikian, and Apostolos P. Georgopoulos; A Simulated Actuator Driven By Motor Cortical Signals; Nov. 1996; NeuroReport 7, pp. 2597–2601.

Venkatesh N. Murthy and Eberhard E. Fetz; Synchronization of Neurons During Local Field Potential Oscillations in Sensorimotor Cortex of Awake Monkeys; Dec., 1996; Journal of Neurophysiology, vol. 76, No. 6; pp. 3968–3982.

A. Rougeul, J.J. Bouyer, L. Dedet, and O. Debray; Fast Somato–Parietal Rhythms During Combined Focal Attention and Immobility in Baboon and Squirrel Monkey; 1979; Electroencephalography and Clinical Neurophysiology, vol. 46, pp. 310–319.

John P. Donoghue, Jerome N. Sanes, Nicholas G. Hatsopoulos, and Gyongyi Gaal; Neural Discharge and Local Field Potential Oscillations in Primate Motor Cortex During Voluntary Movements; Journal of Neurophysiology, vol. 79, No. 1, Jan. 1998, pp. 159–173.

* cited by examiner

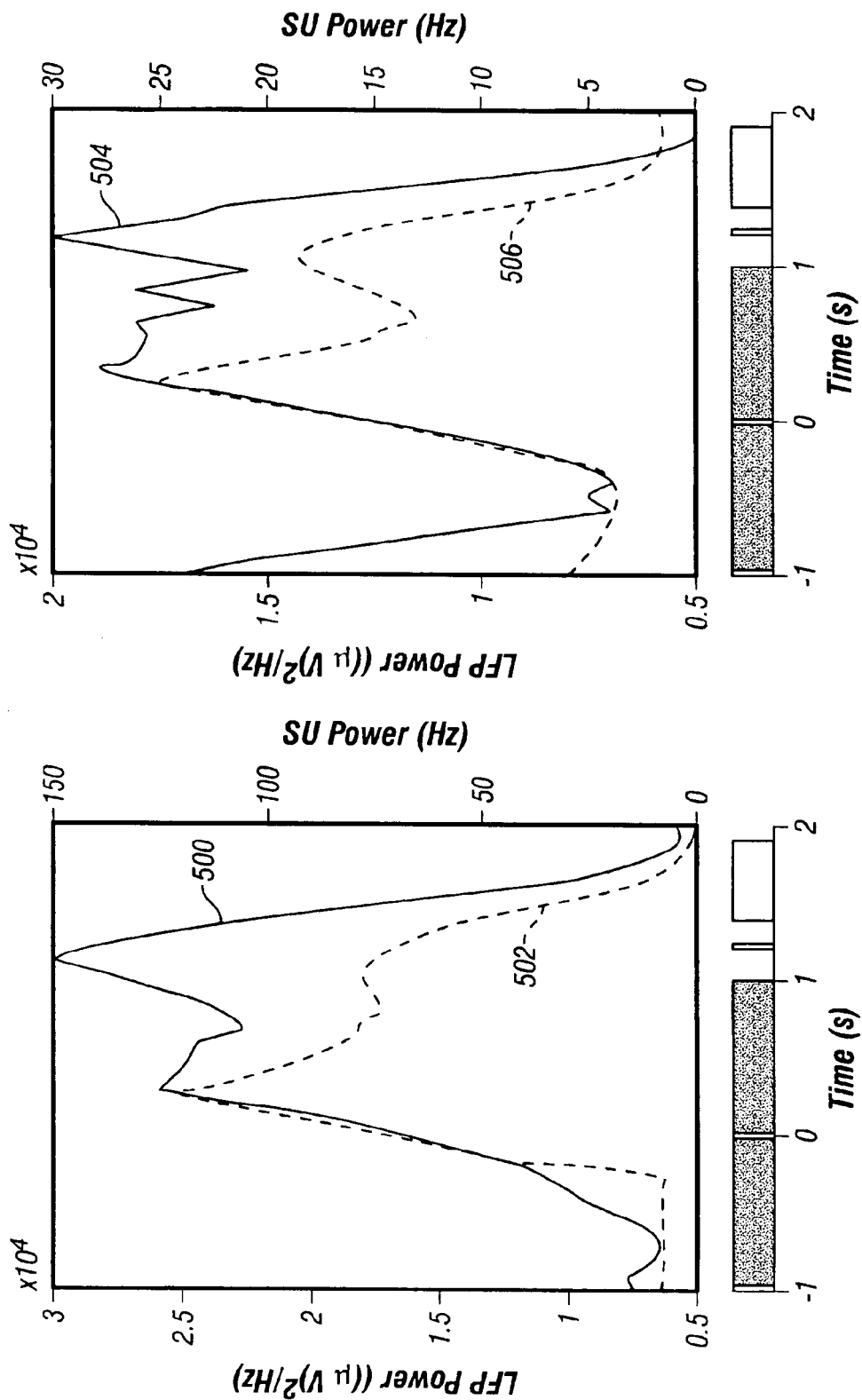

NEURAL PROSTHETIC USING TEMPORAL STRUCTURE IN THE LOCAL FIELD POTENTIAL

CROSS-REFERENCE TO RELATED APPLICATION

This application is a divisional and claims the benefit of priority under 35 USC 120 of U.S. application Ser. No. 09/738,875 filed Dec. 14, 2000, now U.S. Pat. No. 6,615,076, which claims benefit of the priority of U.S. Provisional Application Ser. No. 60/170,861 filed Dec. 14, 1999, and entitled "A Neural Prosthetic Using Temporal Structure in the Local Field Potential".

NOTICE OF GOVERNMENT CONTRACT

The U S. Government has certain rights in this invention pursuant to Grant No. EY05522-22 awarded by the National Institute of Health and Grant No. N00014-94-0412 awarded by the Office of Naval Research.

BACKGROUND

Many limb prostheses operate in response to muscle contractions performed by the user. Some prostheses are purely mechanical systems. For example, a type of lower limb prosthesis operates in response to the motion of the residual limb. When the user's thigh moves forward, inertia opens the knee joint of the prosthesis, an artificial shin swings forward, and, when the entire structure locks, the user may pass his or her weight over the artificial leg. Other prostheses may incorporate electric sensors to measure muscle activity and use the measured signals to operate the prosthesis.

Such prostheses may provide only crude control to users that have control over some remaining limb musculature, and hence may not be useful for patients with spinal damage. For these patients, it may be desirable to measure precursor signals coded for limb movement in the patient's brain, and then decode these signals to determine the intended movement and/or target. The decoded signals could be used to operate a pointing device on a computer display screen or robotic prosthesis.

BRIEF DESCRIPTION OF THE DRAWINGS

FIGS. 5A and 5B are plots showing the dynamics of 70 Hz power in SU and LFP activity.

DETAILED DESCRIPTION

Figure 1:
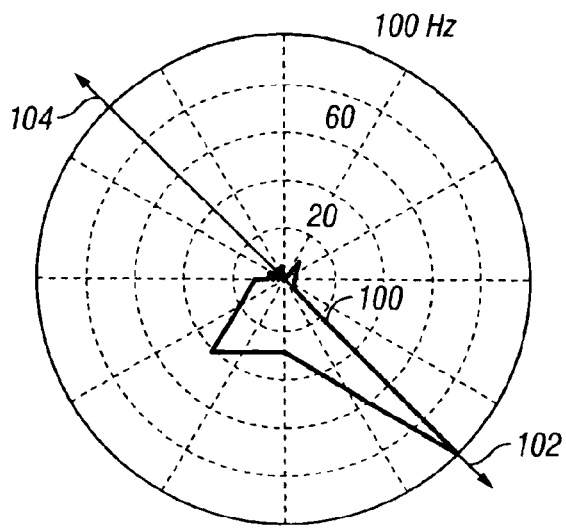
FIG. 1 is a graph illustrating spatial tuning of a neuron in a test subject.

An electrode may be implanted into the cortex of a subject and used to measure the signals produced by the firing of a single unit (SU), i.e., a neuron, in the vicinity of an electrode. The SU signal may contain a high frequency component. This component may contain spikes—distinct events that exceed a threshold value for a certain amount of time, e.g., a millisecond. Spikes may be extracted from the signal and sorted using known spike sorting methods.

Attempts have been made to use the spike trains measured from particular neurons to predict a subject's intended movements. The predicted intention could then be used to control a prosthetic device. However measuring a spike train with a chronic implant and decoding an intended movement in real time may be complicated by several factors.

In general, measuring SU activity with a chronic implant may be difficult because the SU signal may be difficult to isolate. An electrode may be in the vicinity of more than one neuron, and measuring the activity of a target neuron may be affected by the activity of an adjacent neuron(s). The implant may shift position in the patient's cortex after implantation, thereby changing the proximity of an electrode to recorded neurons over time. Also, the sensitivity of a chronically implanted electrode to SU activity may degrade over time.

Local field potential (LFP) is an extracellular measurement that represents the aggregate activity of a population of neurons. The LFP measured at an implanted electrode during the preparation and execution of a task has been found to have a temporal structure that is approximately localized in time and space. Information provided by the temporal structure of the LFP of neural activity appears to correlate to that provided by SU activity, and hence may be used to predict a subject's intentions. Unlike SU activity, measuring LFP activity does not require isolating the activity of a single unit. Accordingly, it may be advantageous to use LFP activity instead of, or in conjunction with SU activity to predict a subject's intended movement in real time.

Temporal structure is a general term that describes patterns in activity over time. Temporal structure localized in both time and frequency involves events that repeat approximately with a period, T, during a time interval, after which the period may change. For example, the period may get larger, in which case the frequency could get smaller. However, for the temporal structure to remain localized in frequency as it changes in time, large changes in the frequency of events cannot occur over short intervals in time.

The relationship between LFP and SU activity in the lateral intraparietal (LIP) cortex, responsible for eye movement, was studied in an experiment. Neural activity in LIP was recorded in two adult male Rhesus monkeys while performing a memory-saccade task. The neural activity was recorded using single tetrodes.

Each trial of the memory-saccade task began with illuminating a central fixation light to which the animal saccaded. The animal was required to maintain fixation within a 2° circular window while the fixation light was present.

After a period of one to two seconds, a target light was flashed for 100 milliseconds at one of eight fixed stimulus locations evenly distributed on a 10° circle. Following the target flash, the monkey had to remain fixated for a period of one second, at the end of which the fixation light was extinguished and the animal was required to saccade to the remembered location of the flashed stimulus. For accurate saccades, the target was re-illuminated for a minimum of 500 milliseconds, often triggering a corrective saccade, and the animal was required to fixate at the new location while the target light remained on. Target locations were randomly interleaved to collect between ten to fifteen successful trials for each location in blocked fashion.

The response of a neuron in the movement planning areas of the cortex, for example, the LIP, may be "tuned" to a particular direction, that is, the neuron may fire at a higher rate when a movement is planned in a preferred direction than in other directions. For example, FIG. 1 illustrates the firing frequency response 100 of a neuron in the parietal reach region (PRR) of a monkey over a 360 degrees of reach directions. The PRR is responsible for the high level planning of reaches. This neuron fires at a maximum rate of about 100 Hz when the monkey plans a reach in the preferred direction 102. The direction opposite the preferred direction is referred to as the anti-preferred direction 104.

Figure 2A:
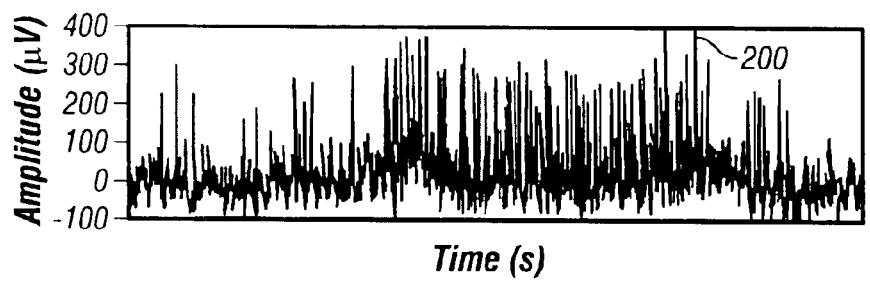
FIGS. 2A and 2B are graphs of waveforms measured by an electrode in response to an impending movement.
Figure 2B:
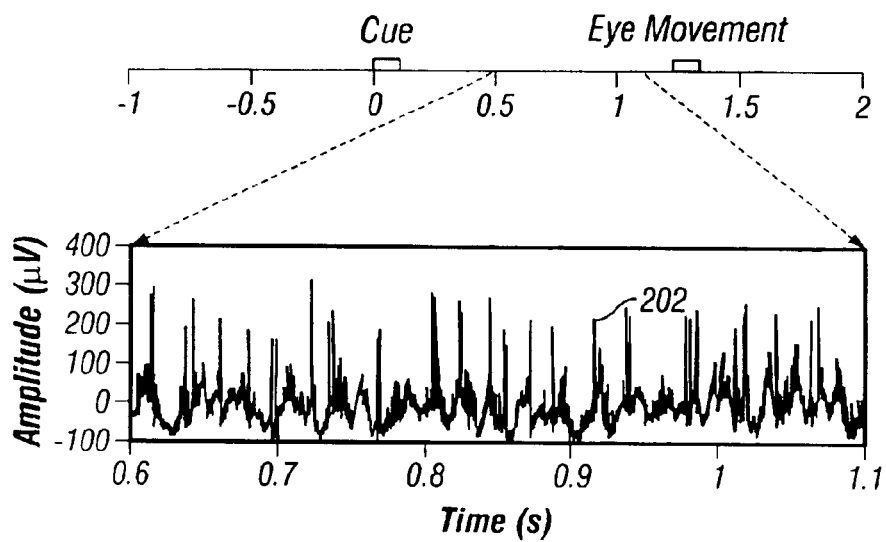

Recorded neural signals were amplified and filtered before being digitized. Digital data was then streamed to a disk. Waveforms such as that shown in FIG. 2A were recorded during memory saccade tasks. FIG. 2B shows a portion 202 of the waveform 200 of FIG. 2A on an expanded time base.

SU activity, i.e., spike trains, and the LFP were calculated from the recorded neural activity. Both the SU and LFP data were found to have temporal structure that exhibited directional tuning. Furthermore, coherency between SU and LFP activity was found to be highly significant in a gamma band (25–90 Hz) of the SU and LFP activity. Also, single units exhibited phase locking to the LFP and preferentially fired at the peak of an LFP oscillation throughout the memory period.

Figure 3A:
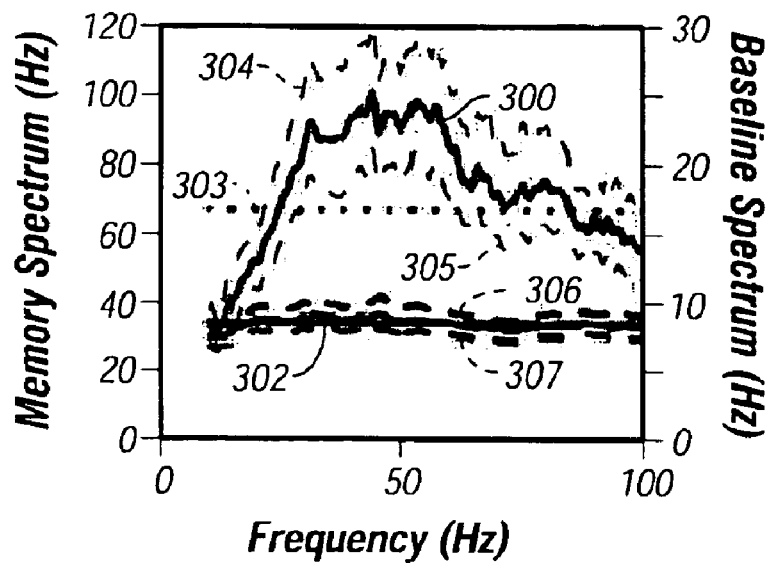
FIG. 3A is a plot showing the spectral structure of single unit (SU) activity.

FIG. 3A shows individual spectra of SU activity in the preferred direction for a single cell from one monkey. FIG. 3A illustrates the spectrum of SU activity during the memory period 300 and baseline period 302 from a typical SU. The high frequency limit of the spectrum in each case is shown by dotted line 303. Ninety-five percent error bars are shown by thin dotted lines 304–307.

The spectrum of a Poisson process with the same firing rate would fall on the high-frequency limit line 303. Therefore deviations of the spectrum from this line are evidence of temporal structure.

Two significant features are present in the memory period spectrum that are absent from the baseline period. This indicates the presence of temporal structure during working memory. The first significant feature is a suppression in power at frequencies below 20 Hz. The second is a peak in power at a higher frequency band, in this case centered at 50 Hz.

Figure 3B:
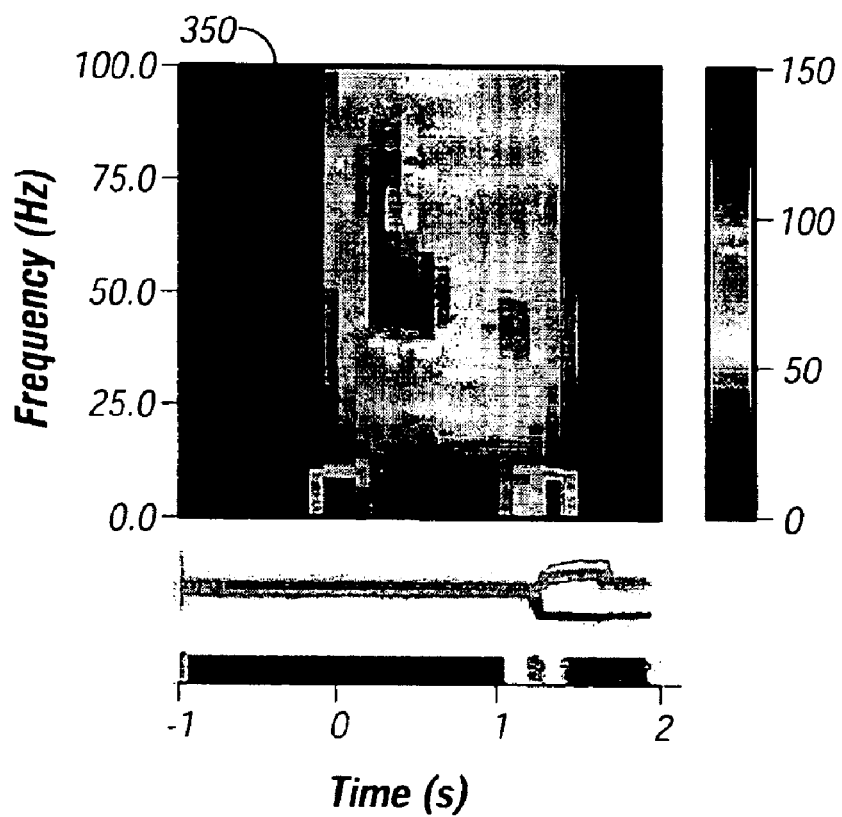
FIG. 3B is a spectrogram of the spectral structure shown in FIG. 3A.

FIG. 3B shows a spectrogram 300 for the same unit shown in FIG. 3A. The spectrogram 300 presents the spectrum as a function of time. As shown in FIG. 3A, the spectral structure is sustained throughout the memory period, beginning at the initial target illumination and continuing though the saccade.

Figure 4:
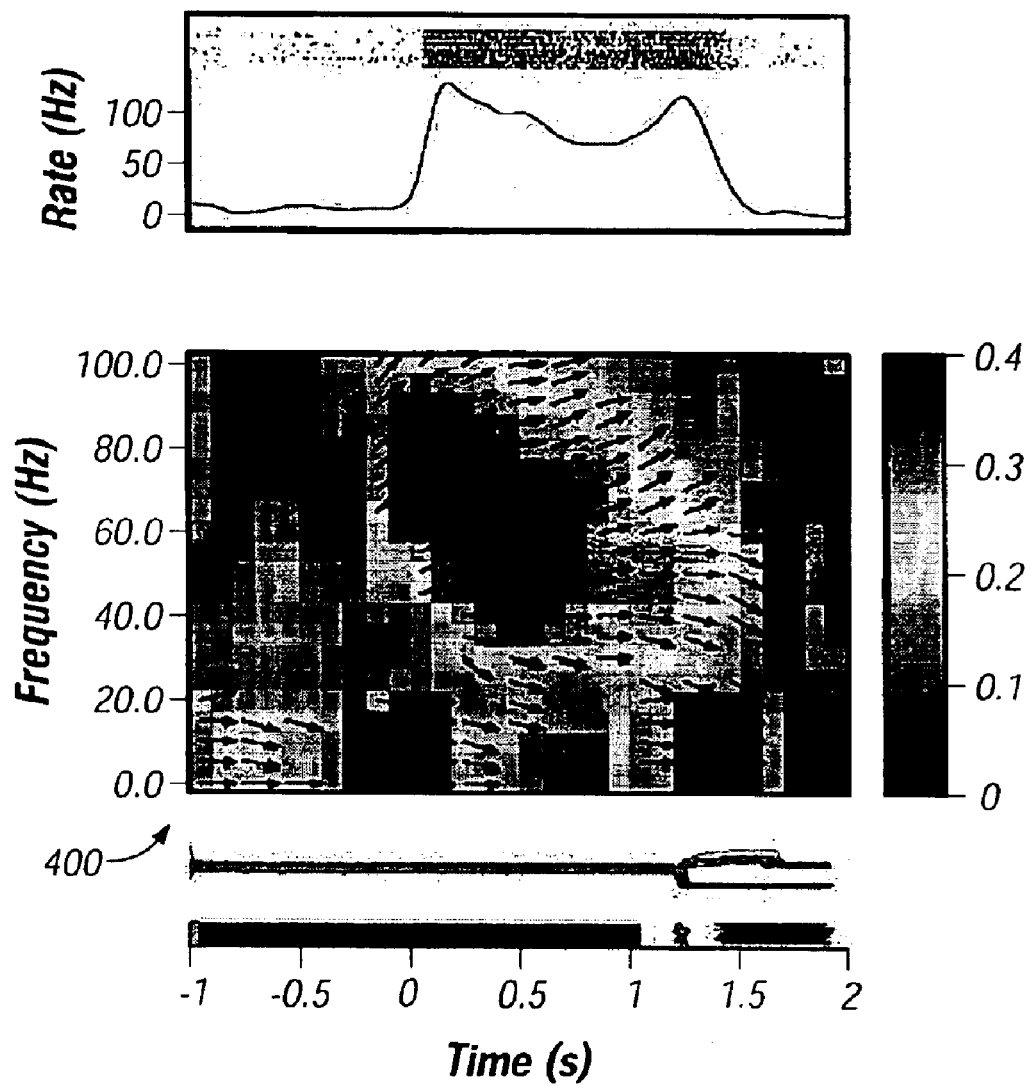
FIG. 4 is a two-dimensional plot showing the time-frequency coherence between SU and local field potential (LFP) spectra.

FIG. 4 is a spectrograph 400 that shows the coherency between a single cell and the simultaneously recorded LFP averaged across all trials to the preferred direction. A sharp increase in the coherence between SU activity and the LFP can be seen at 70±20 Hz that exceeds 99% confidence intervals. This increase is sustained through the memory period. When the coherence is significant the phase of the coherency is also well-organized in this band and has a value of zero radians. This is evidence for phase-locking between the SU and the LFP during working memory that is sustained throughout the period. In particular, the phase of the coherency indicates that during working memory, the SU fires at the peak of broad-band 25–90 Hz LFP activity. In a given window, the phase of the coherency is relatively constant across frequency indicating that SU and gamma band activity are synchronous with no time lag between them.

Since the power in each process is explicitly normalized, the increase in coherence during the memory period is not related to power increases in either process. Instead, it is a result of an increase in the predictability of one process given the other. This indicates that predicting when the single unit will fire from LFP activity may be more accurate during working memory than during simple fixation.

Comparing the power in SU and LFP activity at a particular frequency band over time and across trial conditions reveals similar organization during the task. FIGS. 5A and 5B show the dynamics of power of neuronal activity in the 70±20 Hz frequency band. FIG. 5A illustrates the LFP 500 and SU 502 gamma band activity from a single cell, and FIG. 5B illustrates the population average of LFP 504 and SU 506 activity in one monkey.

Figure 6B:
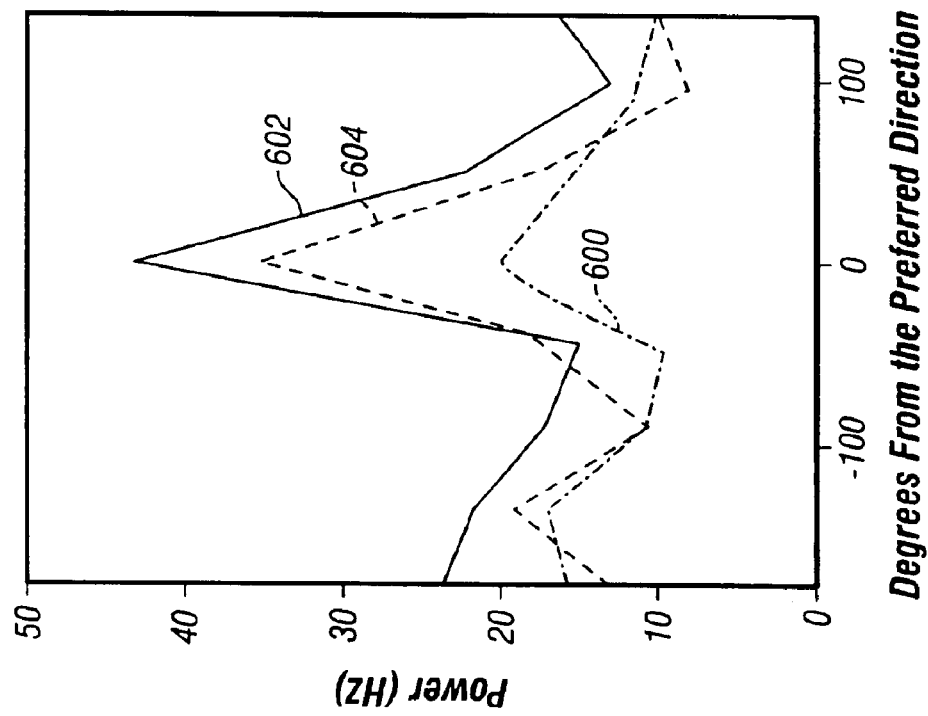
FIGS. 6A and 6B are plots showing tuning of 70 Hz power in LFP and SU activity.
Figure 6A:
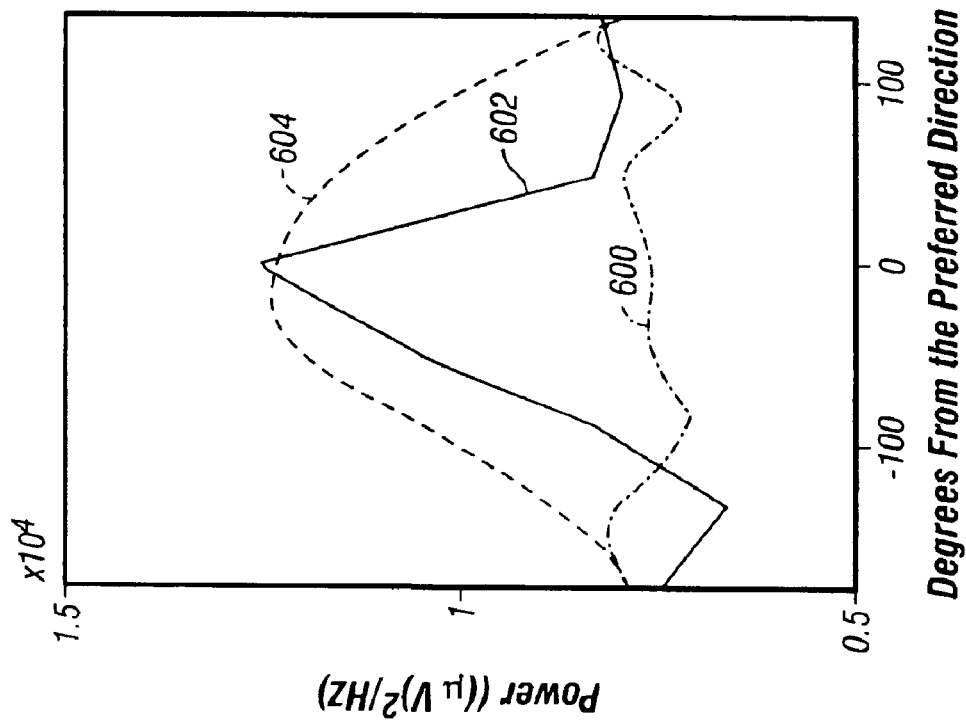

FIGS. 6A and 6B compare LFP and SU activity in the 70±10 Hz band in the preferred direction during the task. The baseline 600, memory 602, and perisaccade 604 activity is show against saccade direction. The preferred direction is aligned toward the center of the plot in each case. Elevations in SU activity at 70±10 Hz are mirrored in the LFP throughout the task, and both show strong directional tuning.

Figure 7B:
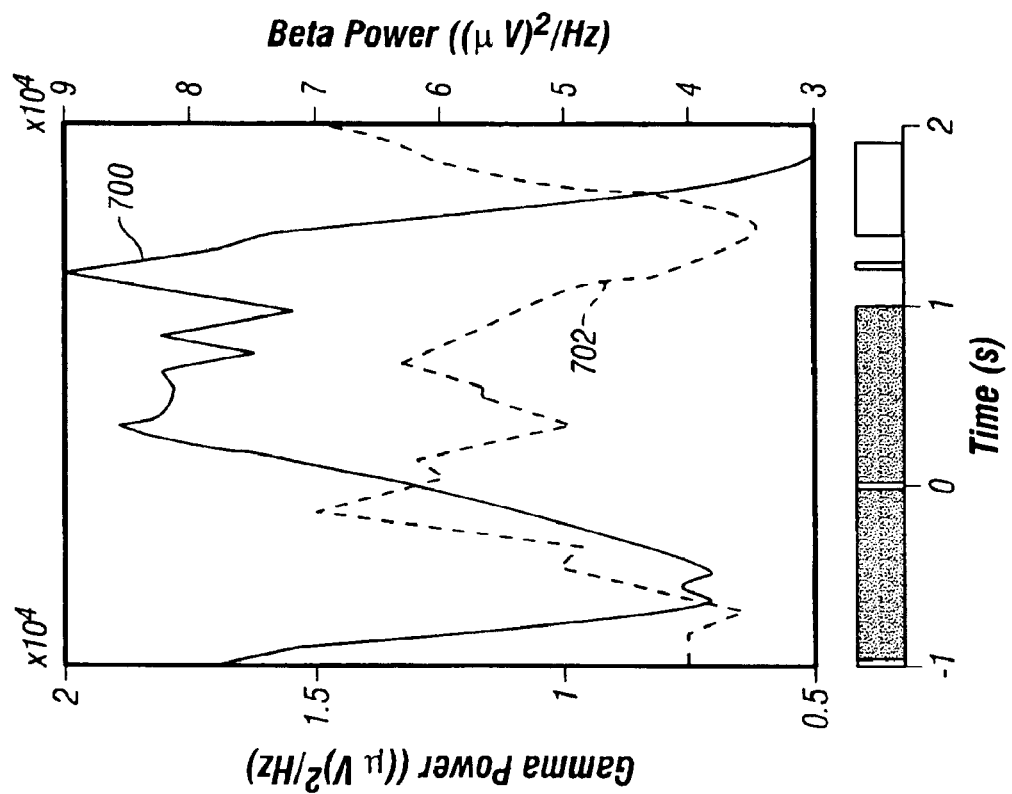
FIGS. 7A and 7B are plots showing dynamics of LFP power at 70 Hz and 20 Hz.
Figure 7A:
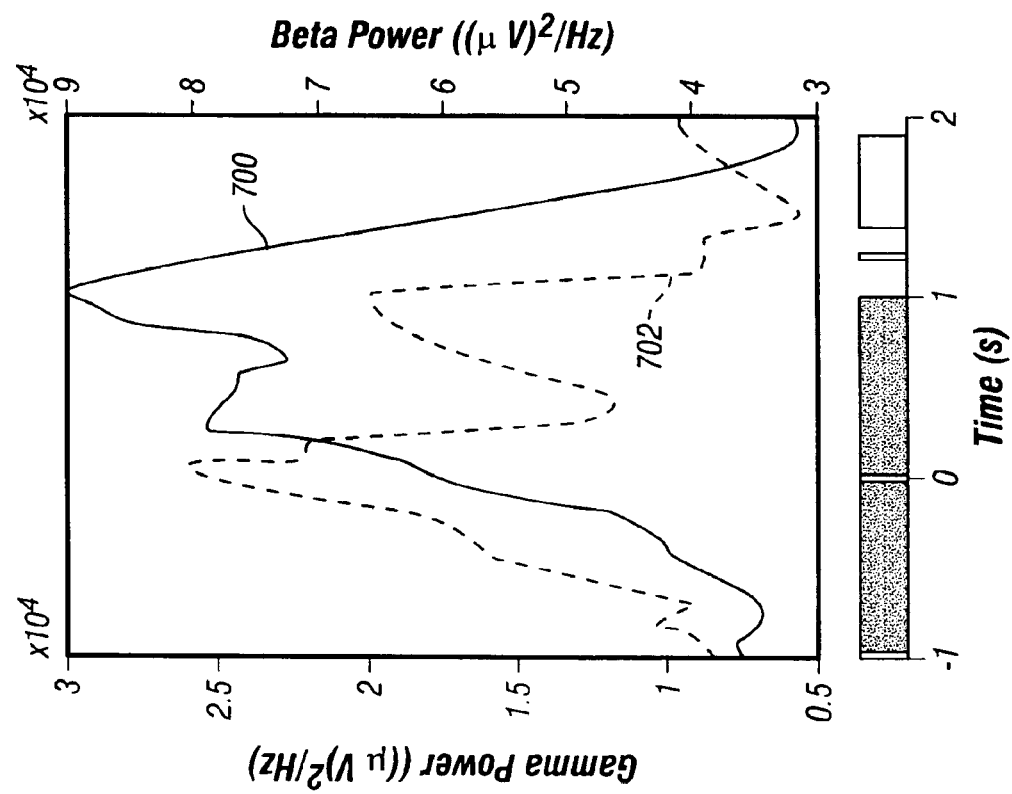

LFP activity between a frequency band 700 at 70±10 Hz and a frequency band 702 at 20±5 Hz for trials with saccades to the preferred directions are compared for a single site and a population average in FIGS. 7A and 7B, respectively. Activity at 70 Hz is elevated from the initial target onset through the saccade. Activity at 20 Hz rises toward the end of the memory period and is suppressed peri-saccadically. The elevated 70 Hz activity may be related to movement planning. The suppression in 20 Hz activity peri-saccadically may be related to movement execution. The rise in 20 Hz activity toward the end of the memory period may reflect preparatory aspects of the task and the decrease at the end of the memory period may reflect a "go" signal that indicates a decision to execute the planned movement.

Figure 8:
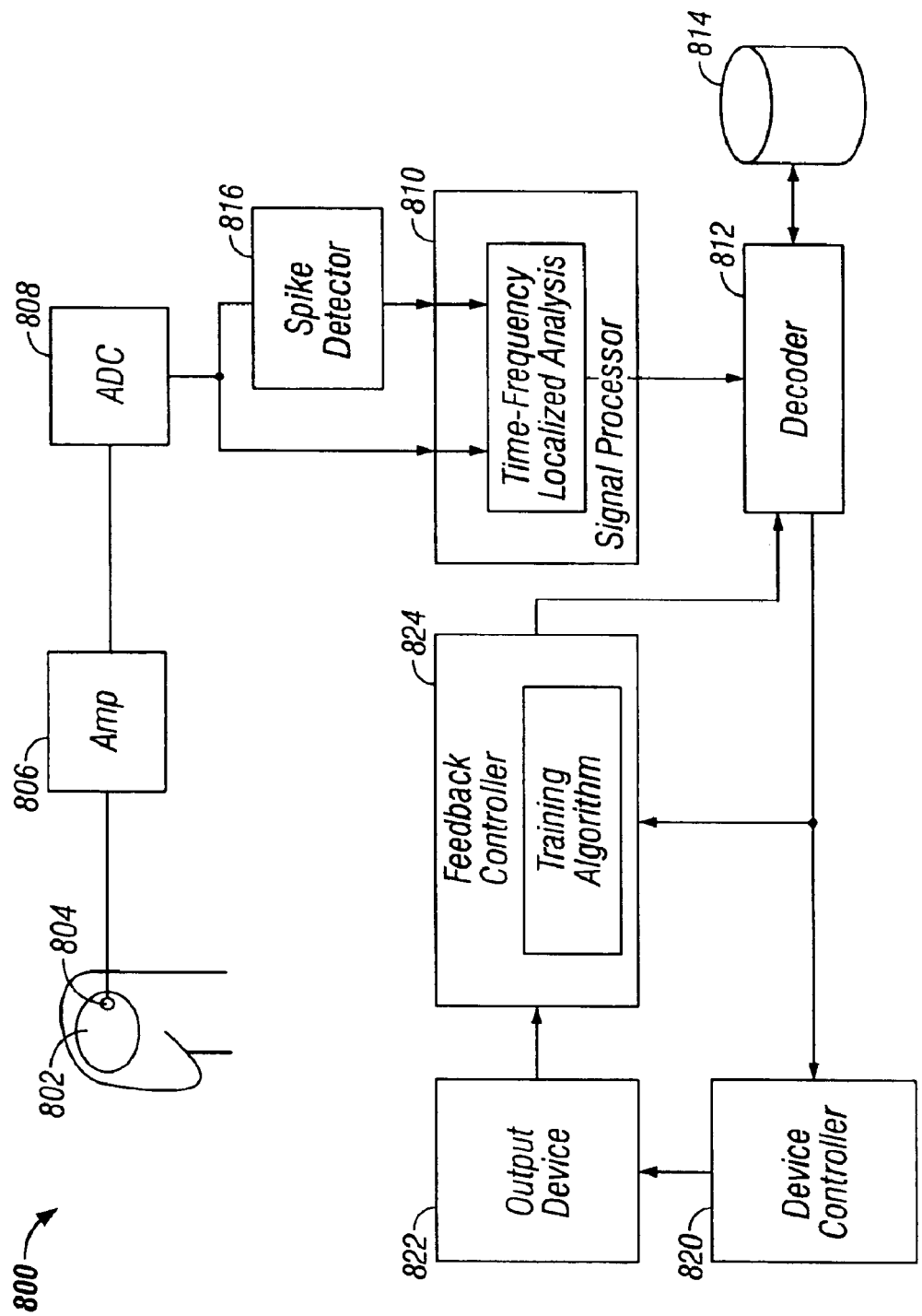
FIG. 8 is a schematic diagram of a system according to an embodiment.
Figure 9:
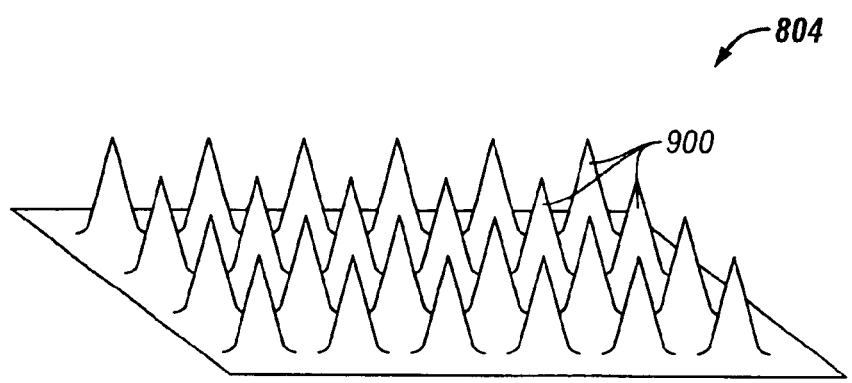
FIG. 9 illustrates perspective view of an implant according to an embodiment.

FIG. 8 illustrates a system 800 that uses LFP activity to predict a subject's intended movement plan. The activity of neurons in the subject's brain 802 may be recorded with an implant 804, such as that shown in FIG. 9. The implant 804 may include an array of electrodes 900 that measure the action potential (SU) and extracellular potential (LFP) of cells in their vicinity. In alternate embodiments, the neural activity may be measured in forms other than electrical activity. These include, for example, optical or chemical changes, or changes in blood flow that may be measured by suitable measuring devices.

Figure 10:
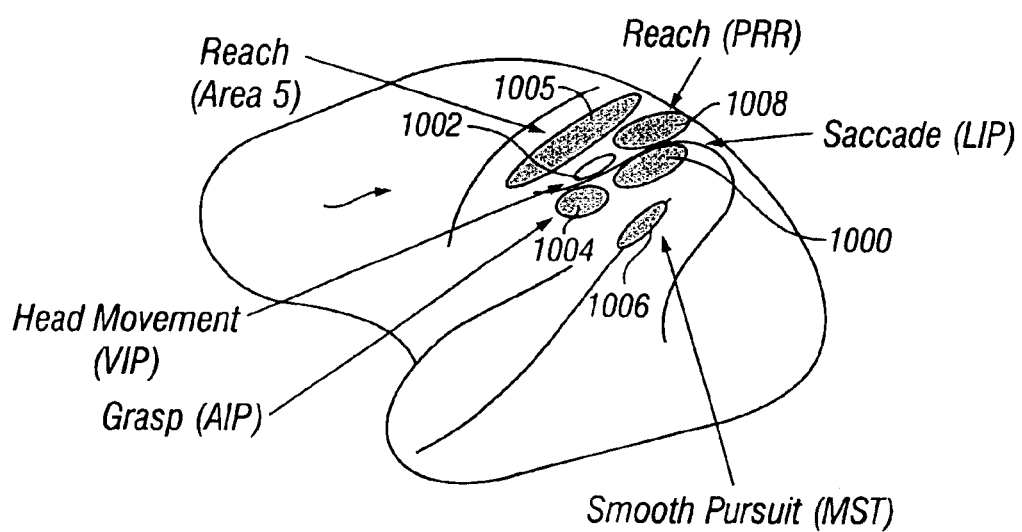
FIG. 10 is a plan view of a subject brain illustrating implant sites according to an embodiment.

FIG. 10 illustrates a number of exemplary implant sites. The implant 804 may be implanted at different sites for decoding different movements. For example, reaches are coded in the parietal reach region (PRR) and area 5 of the superior parietal lobule 1005, saccades are encoded in the LIP 1000, head movements in the ventral intraparietal (VIP) cortex 1002, grasps in the anterior intraparietal (AIP) cortex 1004, and smooth pursuit eye movements in the medial superior temporal (MST) cortex 1006. Reach and other body movements may be encoded in other areas of the sensory motor cortex. These areas may include, for example, frontal cortical areas involved in movement, such as the motor cortex, ventral and dorsal premotor cortex, supplementary motor area, supplementary eye field, frontal eye field, prefrontal cortex, and pre-supplementary motor area.

The PRR 1008 may be a desirable site for a neural implant used to decode reaches. The PRR generates high-level plans for reaching that may require fewer neurons to read out the overall goal of a planned movement than may be required in other areas. PRR neurons code the target of a reach in eye-centered coordinates rather than limb-centered coordinates. Also, the PRR neurons code only the goal of the movement, and appear to code only the next planned movement in a sequential reach task.

The PRR may also undergo less reorganization after acute nerve damage. The removal of an arm or leg or a spinal cord injury may cause grand-scale functional reorganization of cortical maps in both the somatosensory and motor cortices. Since the major input to the PRR appear to be derived from the visual system, which may remain intact in paralyzed patients, the PRR may undergo less reorganization than the somatosensory and motor cortices in these patients.

Neural activity measured with the implant 804 may be amplified in one or more amplifier stages 806 and digitized by an analog-to-digital converter (ADC) 808. In an embodiment, multiple implants may be used. Recordings may be made from multiple sites in a brain area, with each brain site carrying different information, e.g., different directions of planned movement. The signals recorded from different implants may be conveyed on multiple channels.

The measured waveform(s), which may include frequencies in a range having a lower threshold of about 1 Hz and an upper threshold of from 5 kHz to 20 kHz may be filtered as an analog or digital signal into different frequency ranges. For example, the waveform may be filtered into a low frequency range of say 1–20 Hz, a mid frequency range of say 15–200 Hz, which includes the beta (15–25 Hz) and gamma (25–90 Hz) frequency bands, and a high frequency range of about 200 Hz to 1 kHz, which may include unsorted spike activity.

In an alternate embodiment, the digitized signal may also be input to a spike detector 816 which may detect and sort spikes using known spike sorting operations.

The digitized LFP signal, and the sorted spike signal if applicable, may be input to a signal processor 810 for time-frequency localized analysis.

Figures 11A, 11B:
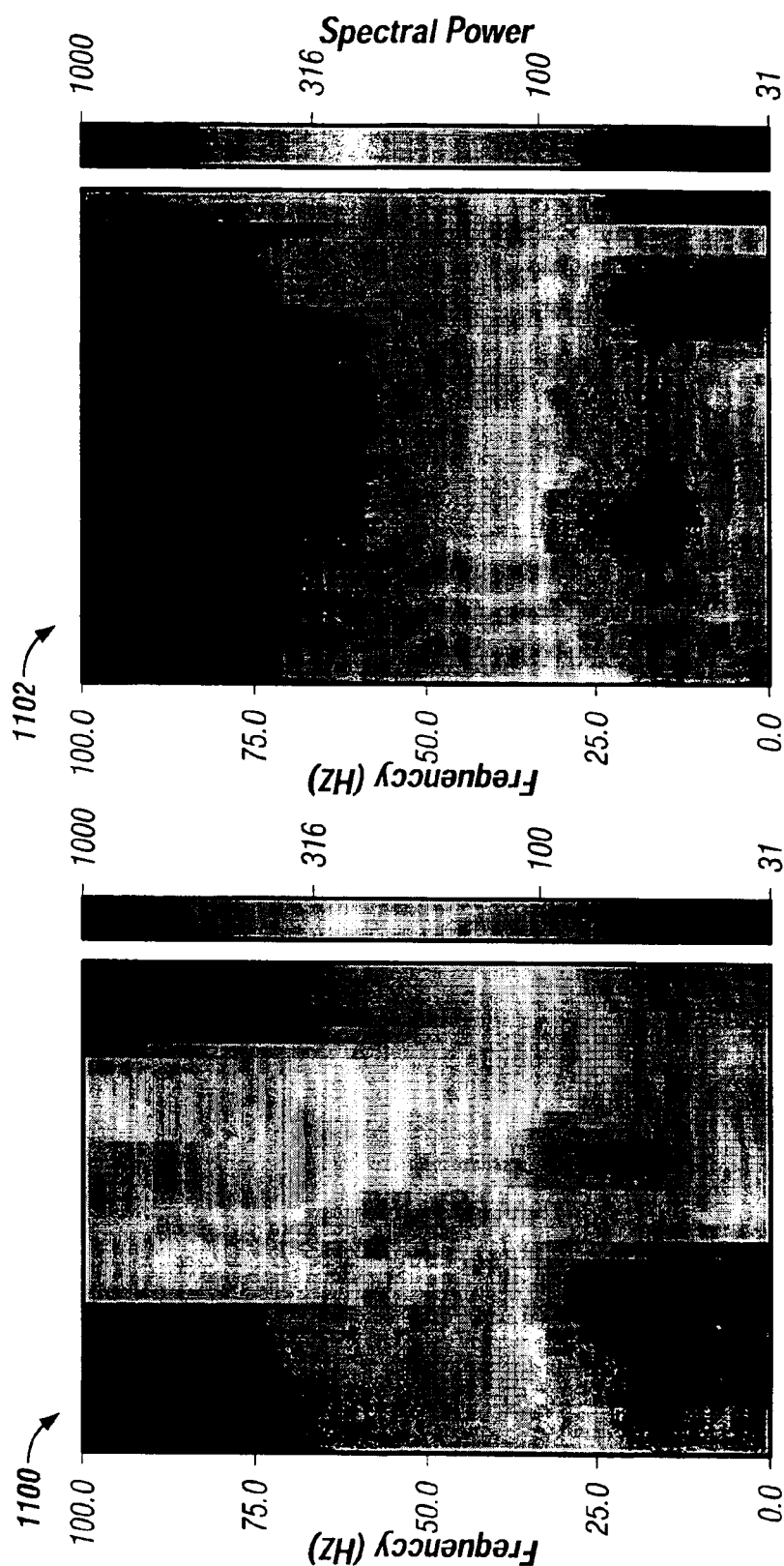
FIGS. 11A and 11B are spectrographs showing the spectral structure of LFP signals recorded in a preferred and an anti-preferred direction, respectively.

The digitized LFP and spike (SU) signals may be represented as spectrograms. For example, FIGS. 11A and 11B illustrate spectrograms 1100, 1102 of LFP activity in a preferred and an anti-preferred direction obtained in an experiment, and demonstrate the directional tuning of the LFP activity. The spectrograms may be estimated by estimating the spectrum for the data in a time window, translating the window a certain distance in time, and repeating. Although SU activity is a point process composed of discrete events in time (action potentials) in contrast to continuous processes such as the LFP that consist of continuous voltage changes, both may be analyzed using similar methods.

The signal processor 810 may estimate the spectral structure of the digitized LFP and spike signals using multitaper methods. Multitaper methods for spectral analysis provide minimum bias and variance estimates of spectral quantities, such as power spectrum, which is important when the time interval under consideration is short.

With multitaper methods, several uncorrelated estimates of the spectrum (or cross-spectrum) may be obtained from the same section of data by multiplying the data by each member of a set of orthogonal tapers. A variety of tapers may be used. Such tapers include, for example, Parzen, Hamming, Hanning, Cosine, etc.

In an embodiment, the Slepian functions are used. The Slepian functions are a family of orthogonal tapers given by the prolate spheroidal functions. These functions are parameterized by their length in time, T, and their bandwidth in frequency, W. For choice of T and W, up to K=2TW−1 tapers are concentrated in frequency and are suitable for use in spectral estimation.

For an ordinary time series, $x_t$, t=1, ..., N. The basic quantity for further analysis is the windowed Fourier transform $\tilde{x}_k^{(X)}(f)$:

$$\tilde{x}_k^{(X)}(f) = \sum_{1}^{N} w_t(k) x_t \exp(-2\pi i f t)$$

where $w_t(k)$ (k=1, 2, ..., K) are K orthogonal taper functions.

For the point process, consider a sequence of event times $\{\tau_j\}$, j=1, ..., N in the interval [0,T]. The quantity for further analysis of point processes is also the windowed Fourier transform, denoted by $\tilde{x}_k^{(N)}(f)$:

$$\tilde{x}_k^{(N)}(f) = \sum_{j=1}^{N} w_{\tau_j}(k) \exp(-2\pi i f \tau_j) - \frac{N(T)}{T} \tilde{w}_0(k)$$

where $w_0(k)$ is the Fourier transform of the data taper at zero frequency and N(T) is the total number of spikes in the interval.

When averaging over trials we introduce an additional index, I, denoting trail number $\tilde{x}_{k,i}(f)$.

When dealing with either point or continuous process, the multitaper estimates for the spectrum $S_x(f)$, cross-spectrum $S_{yx}(f)$, and coherency $C_{yx}(f)$ may be given by:

$$S_x(f) = \frac{1}{K} \sum_{k=1}^{K} |\tilde{x}_k(f)|^2$$

$$S_{yx}(f) = \frac{1}{K} \sum_{k=1}^{K} |\tilde{y}_k(f) \tilde{x}_k^*(f)|$$

$$C_{yx}(f) = \frac{S_{yx}(f)}{\sqrt{S_x(f) S_y(f)}}$$

The auto- and cross-correlation functions may be obtained by Fourier transforming the spectrum and cross-spectrum.

In an alternate embodiment the temporal structure of the LFP and SU spectral structures may be characterized using other spectral analysis methods. For example, filters may be combined into a filter bank to capture temporal structures localized in different frequencies. As an alternative to the Fourier transform, a wavelet transform may be used to convert the date from the time domain into the wavelet domain. Different wavelets, corresponding to different tapers, may be used for the spectral estimation. As an alternative to calculating the spectrum on a moving time window, nonstationary time-frequency methods may be used to estimate the energy of the signal for different frequencies at different times in one operation. Also, non-linear techniques such as artificial neural networks (ANN) techniques may be used to learn a solution for the spectral estimation.

The signal processor 810 may generate a feature vector train, for example, a time series of spectra of LFP, from the input signals. The feature vector train may be input to a decoder 812 and operated on to predict the subject's intended movement, and from this information generate a high level control signal.

The decoder 812 may use different predictive models to predict the intended movement. These may include, for example: probabilistic; Bayesian decode methods (such those described in Zhang, K., Ginzburg, I., McNaughton, B. L., and Sejnowski, T. J. (1998), *Interpreting Neuronal Population Activity by Reconstruction: Unified Framework with Application to Hippocampal place cells.* J Neurophysiol 79:1017–1044); population vector models (such as those described in Lukashin, A. V., Amirikian, B. R., and Georgopoulos, A. P. (1996). *A Simulated Actuator Driven by Motor Cortical Signals.* Neuroreport 7(15–17):2597–2601); and artificial neural networks.

The decoder 812 may use a derived transformation rule to map a measured neural signal, s, into an action, a, for example, a target. Statistical decision theory may be used to derive the transformation rule. Factors in the derivations may include the set of possible neural signals, S, and the set of possible actions, A. The neuro-motor transform, d, is a mapping for S to A. Other factors in the derivation may include the intended target θ and a loss function which represents the risk associated with taking an action, a, when the true intention was θ. These variables may be stored in a memory device, e.g., a database 814.

Two approaches may be used to derive the transformation rule: A probabilistic approach, involving the intermediate step of evaluating a probabilistic relation between s and θ and subsequent minimization of an expected loss to obtain a neuro-motor transformation; and a direct approach, involving direct construction of a neuro-motor transformation and minimizing the empirical loss evaluated over the training set. In terms of so called 'neural network' functions, the second approach may be regarded as defining a neural network with the neural signals as input and the target actions as output, the weights being adjusted based on training data. In both cases, a critical role is played by the loss function, which is in some sense arbitrary and reflects prior knowledge and biases of the investigator.

As described above, the measured waveform(s) may be filtered into a low frequency range of say 1–20 Hz, a mid frequency range of say 15–200 Hz, which includes the beta (15–25 Hz) and gamma (25–90 Hz) frequency bands, and a high frequency range of about 200 Hz to 1 kHz, which may include unsorted spike activity. The decoder 812 may decode an intended direction using the information in the gamma frequency band (25–90 Hz) of the LFP spectra and the SU spectra. The decoder 812 may decode logical signals using information in the gamma (25–90 Hz) and beta (15–25 Hz) frequency bands of the LFP spectra and the SU spectra. The logical information may include a decision to execute an action, e.g., a "go" signal. The logical information may indicate that the subject is entering other states, such as cuing a location, preparing to execute an action, and scrubbing a planned action.

Figure 12:
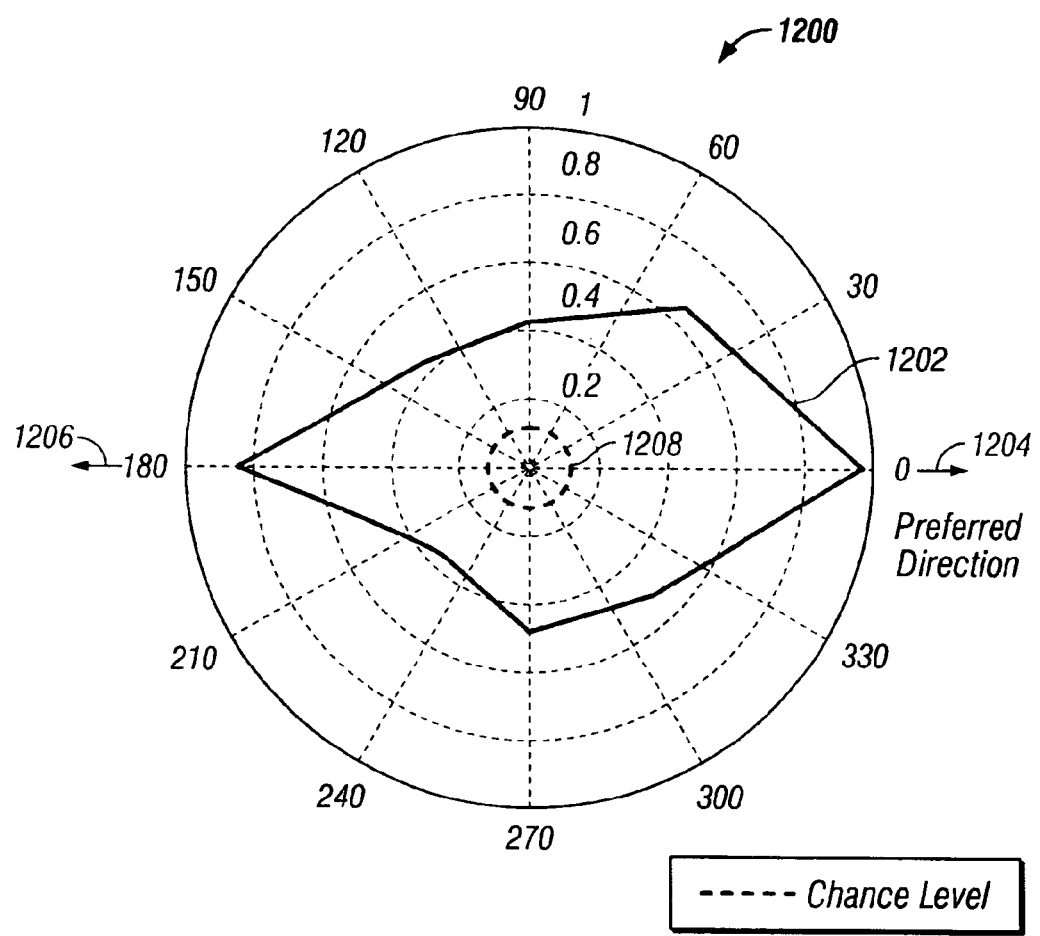
FIG. 12 is a plot showing a direction decode.

In an experiment, the decoder decoded a direction for a saccade and differentiated the planning and the execution periods of the saccade. FIG. 12 is a polar plot of a direction decode 1200 (for one of eight directions) using the LFP at a single site in LIP. Saccade direction is shown on a circle, and the fraction correct 1202 is given by the radius of the point. The decode was based on Fisher's linear discriminant trained with ten trials to each saccade direction for a total of eighty trials. The feature space was three dimensional, given by the value of the spectrum estimated on a 500 millisecond window at frequencies in the gamma frequency band. The frequencies that gave the best decode performance were chosen. As shown in FIG. 12, the LFP at a single site can predict saccades to the preferred direction 1106 and the anti-preferred direction 1208 for that site well, and all other directions better than chance 1208.

Figure 13:
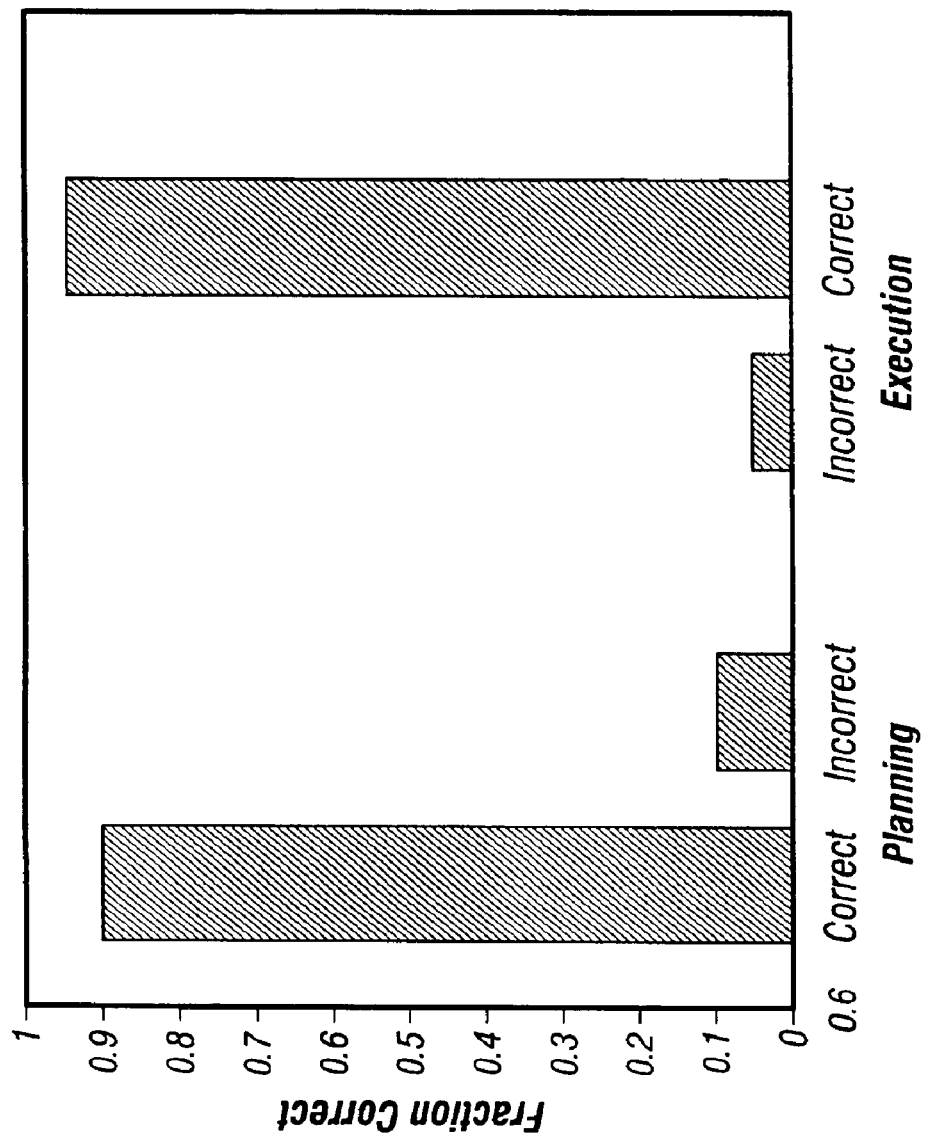
FIG. 13 is a bar graph showing a decode of planning versus execution periods.

FIG. 13 is a bar graph representing a decode 1200 of the planning versus execution periods of the trial using the LFP. The decoder had to determine whether the data came from the planning or execution period of the trial, regardless of saccade direction. The decoder was based on Fisher's linear discriminant trained with eighty trials from each of the two trial periods for a total of 160 samples. The feature space was four dimensional given by power in the beta and gamma frequency bands. As shown in FIG. 13, the decoder predicted the period correctly in over 90% of the samples.

Once the decoder 812 maps the feature vectors from the signal processor 810 to an action, the decoder 812 may generate a high level signal indicative of the intended movement and transmit this signal to the device controller 820. The device controller 820 may use the signal to control the output device 822 to mimic the subject's intended movement. The output device may be, for example, a robotic limb, an animated limb or a pointing device on a display screen, or a functional electrical stimulation device implanted into the subject's muscles for direct stimulation and control.

The decoder 812 may need to be recalibrated over time. This may be due to inaccuracies in the initial calibration, degradation of the implant to spike activity over time, and/or movement of the implant, among other reasons.

In an embodiment, the decoder 812 may use a feedback controller 824 to monitor the response of the output device, compare it to the predicted intended movement, and recalibrate the decoder 812 accordingly. The feedback controller 824 may include a training program to update a loss function variable used by the decoder 812.

Some error may be corrected as the subject learns to compensate for the system response based on feedback provided by watching the response of the output device. The degree of correction due to this feedback response, and hence the amount of recalibration that must be shouldered by the system 800, may depend in part on the degree of plasticity in the region of the brain where the implant 804 is positioned.

A number of embodiments have been described. Nevertheless, it will be understood that various modifications may be made without departing from the spirit and scope of the invention. Accordingly, other embodiments are within the scope of the following claims.

What is claimed is:

1. A method comprising:
   measuring a local field potential response from neural activity in a subject;

estimating a temporal structure of the measured local field potential response; and generating a signal indicative of an intended movement in response to the estimated temporal structure of said measured local field potential response.

2. The method of claim 1, further comprising:

cueing a subject to perform a plurality of movements;

measuring a local field potential response in response to each of said movements; and storing the local field potential response corresponding to each of said movements in a memory device.

3. The method of claim 2, wherein generating the signal comprises:

comparing the measured local field potential response to a plurality of the stored local field potential responses; and determining the intended movement in response to said comparison.

4. The method of claim 1, wherein the signal comprises an electric signal.

5. The method of claim 1, wherein the measuring is invasive.

6. The method of claim 1, wherein the temporal structure of the measured local field potential response is approximately localized in time and frequency.

7. The method of claim 6, further comprising estimating the temporal structure of using spectral analysis.

8. The method of claim 6, wherein the temporal structure is represented as a spectrogram.

9. The method of claim 1, wherein the intended movement comprises a reach.

10. The method of claim 9, wherein the reach comprises target.

11. The method of claim 9, wherein the reach comprises trajectory.

12. The method of claim 9, wherein the intended movement comprises a grasp.

13. The method of claim 1, wherein the intended movement comprises a saccade.

14. The method of claim 1, wherein the intended movement comprises a head movement.

15. The method of claim 1, wherein the intended movement comprises a smooth pursuit eye movement.

16. The method of claim 1, wherein the intended movement comprises a leg movement.

17. The method of claim 1, wherein the intended movement comprises a go signal.

18. The method of claim 1, wherein the intended movement comprises a scrub signal.

19. The method of claim 1, wherein the neural activity comprises activity in the sensory motor cortex.

20. The method of claim 1, wherein the neural activity comprises activity in the parietal reach region.

21. The method of claim 1, wherein the neural activity comprises activity in the anterior intraparietal cortex.

22. The method of claim 1, wherein the neural activity comprises activity in the lateral intraparietal cortex.

23. The method of claim 1, wherein the neural activity comprises activity in area 5 of the superior parietal lobule.

24. The method of claim 1, wherein the neural activity comprises activity in frontal cortical areas involved in movement, said area selected from the motor cortex, the ventral and dorsal premotor cortex, the supplementary motor area, the supplementary eye field, the frontal eye field, the prefrontal cortex, and the pre-supplementary motor area.

25. The method of claim 1, wherein the neural activity comprises activity in the ventral intraparietal cortex.

26. The method of claim 1, wherein the neural activity comprises activity in the medial superior temporal cortex.

27. The method of claim 1, further comprising decoding a direction in a gamma frequency band of the local field potential response.

28. The method of claim 1, further comprising decoding a logical signal in at least one of a gamma frequency band and a beta frequency band of the local field potential response.

29. The method of claim 28, wherein the logical signal comprises a "go" signal.

30. The method of claim 1, further comprising measuring spike response having a temporal structure approximately localized in time and frequency, and wherein the signal is generated in response to the measured local field potential response and the measured spike response.

31. A method comprising:

measuring neural activity;

analyzing a time and Fourier frequency localized representation of the neural activity; and generating a signal indicative of an intended movement in response to said analysis, wherein the neural activity comprises sorted spiking activity.

32. A method comprising:

measuring neural activity;

analyzing a time and Fourier frequency localized representation of the neural activity; and generating a signal indicative of an intended movement in response to said analysis, wherein the neural activity comprises measuring a local field potential.

33. A method comprising:

measuring neural activity;

analyzing a time and Fourier frequency localized representation of the neural activity; and generating a signal indicative of an intended movement in response to said analysis, wherein the neural activity comprises unsorted spiking activity.

* * * * *